(12) United States Patent
Mork et al.

(10) Patent No.: US 6,627,670 B2
(45) Date of Patent: Sep. 30, 2003

(54) DURABLE, ABSORBENT LATEX FOAM COMPOSITION HAVING HIGH VERTICAL WICKING

(75) Inventors: Steven M. Mork, Midland, MI (US); Andrew T. Graham, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 125 days.

(21) Appl. No.: 09/829,379

(22) Filed: Apr. 9, 2001

(65) Prior Publication Data
US 2002/0002209 A1 Jan. 3, 2002

Related U.S. Application Data

(60) Provisional application No. 60/200,026, filed on Apr. 26, 2000, and provisional application No. 60/230,268, filed on Sep. 6, 2000.

(51) Int. Cl.$^7$ .................................................. C08J 9/30
(52) U.S. Cl. ............................ 521/65; 521/61; 521/64; 521/71
(58) Field of Search ............................ 521/64, 61, 67, 521/71, 65

(56) References Cited

U.S. PATENT DOCUMENTS

| | | |
|---|---|---|
| 3,215,647 A | 11/1965 | Dunn |
| 3,650,995 A | 3/1972 | Erickson |
| 3,887,408 A | 6/1975 | Hoey |
| 3,901,240 A | 8/1975 | Hoey |
| 4,000,028 A | 12/1976 | Hoey |
| 4,069,366 A | 1/1978 | Hoey |
| 4,174,415 A | 11/1979 | Bethe |
| 4,205,103 A | 5/1980 | Davis et al. |
| 4,341,832 A | 7/1982 | Barnett et al. |
| 4,559,243 A | 12/1985 | Passler et al. |
| 4,640,858 A | 2/1987 | Barnett |
| 4,655,210 A | 4/1987 | Edenbaum et al. ......... 128/156 |
| 4,990,541 A | 2/1991 | Nielsen et al. |
| 5,011,864 A | 4/1991 | Nielsen et al. |
| 5,260,345 A | 11/1993 | DesMarais et al. |
| 5,431,970 A | 7/1995 | Broun et al. |
| 5,434,195 A | 7/1995 | Imeokparia et al. |
| 5,550,167 A | 8/1996 | DesMarais |
| 5,741,581 A | 4/1998 | DesMarais et al. |
| 5,763,067 A | 6/1998 | Brüggemann et al. |
| 5,767,168 A | 6/1998 | Dyer et al. |
| 5,782,787 A | 7/1998 | Webster |
| 5,786,395 A | 7/1998 | Stone et al. |
| 6,025,404 A | 2/2000 | Harris et al. |

FOREIGN PATENT DOCUMENTS

| | | |
|---|---|---|
| EP | 0 076 888 A2 | 4/1983 |
| EP | 0 427 219 | 5/1991 |
| EP | 0 642 907 | 3/1995 |
| EP | 0 427 219 B1 | 6/1996 |
| JP | 57-55936 | 4/1982 |
| WO | 98 56430 | 12/1998 |
| WO | 99/02587 | 1/1999 |
| WO | 99 61518 | 12/1999 |

OTHER PUBLICATIONS

Zimmerman, R. L. et al. "Sponge Rubber and Latex Foam", *Plastic Foams Part 1*; K. Frisch and J.H. Saunderd, Editors; Marcel Dekker, Inc. (1972).
Zimmerman, R. L. et al., "Chemically Cured Carboxylated Latex Foam Coating", *Rubber Age*, May 1966, pp. 69–75.
Chemical Abstract, 93:48070v, "Porous Materials", Japan 27,345 (1980).
Chemical Abstract, 93:9370y, "Rubber foams having good water absorption", Japan (1980).
Chemical Abstract, 105:116367r, "Water–absorbent rubber sponge", Japan 91,230 (1986).
Chemical Abstract, 110:136801j, "Preparation of durable water–absorbing rubber", Japan (1988).
Chemical Abstract, 125:303264e, "Dynamic viscoelastic properties of polymer latex films", (1996).
Chemical Abstract, 111:235435v, "Wiping cloths from alveolar cellulosic materials". EP 335,050 (1989).
Kan and Blackson, "Effect of Ionomeric Behavior on the Viscoelastic Properties and Morphology of Carboxylated Latex Films", Macromolecules, vol. 29, No. 21, pp. 6853–6864 (1996).

*Primary Examiner*—Morton Foelak
(74) *Attorney, Agent, or Firm*—Whyte Hirschboeck Dudek SC

(57) ABSTRACT

A durable, conformable, absorbent, hydrophilic, polymeric latex foam composition having a free absorbent capacity of at least 5 grams of a 0.9 weight percent aqueous saline solution per gram of foam and capable of vertically wicking said aqueous saline solution to a height of greater than about 5 cm. In a preferred embodiment, after compression, the latex foam composition remains thin until wet, whereupon it expands and exhibits a high free absorbent capacity and high vertical wicking height.

25 Claims, No Drawings

DURABLE, ABSORBENT LATEX FOAM COMPOSITION HAVING HIGH VERTICAL WICKING

CROSS REFERENCE TO RELATED APPLICATIONS

This application claims the benefit of U.S. application Ser. No. 60/200,026, filed Apr. 26, 2000 and U.S. application Ser. No. 60/230,268, filed Sep. 6, 2000.

BACKGROUND OF THE INVENTION

This invention pertains to an absorbent polymeric foam composition, more specifically, an absorbent, hydrophilic, polymeric latex foam composition. In other aspects, this invention pertains to a method of preparing the absorbent polymeric latex foam composition and to articles fabricated therefrom.

Absorbent, hydrophilic polymeric foams find utility in products which are used for acquiring and distributing aqueous fluids; for example, diapers, adult incontinence pads and briefs; feminine hygiene products, such as, sanitary napkins and tampons; wiping towels and sponges; wound dressings and surgical sponges; clothing apparel, such as, sweat bands and nursing pads; food packaging, such as, absorbent pads for juice and drippings (for example, chicken juice and meat drippings); cable wrap, and water block tape.

Flexible, hydrophilic, nonionic, polymeric foams which are absorbent, that is, capable of acquiring and distributing fluids, are known wherein the foam is prepared by water-in-oil (w/o) high internal phase emulsion (HIPE) polymerization. As examples of this art, refer to the disclosures of U.S. Pat. Nos. 5,550,167, 5,741,581, and 5,786,395. Disadvantageously, the preparation of a polymerized w/o HIPE foam requires processing large volumes of water, which complicates the foam production process. Moreover, obtaining a dry foam from a w/o HIPE polymerization is difficult. As a further disadvantage, HIPE foams typically require post-synthesis functionalization or rinse treatments in order to render the foam hydrophilic and therefore capable of absorbing aqueous fluids. U.S. Pat. No. 5,741,581 further discloses that the polymeric foam material may be "collapsible," but expandable upon contact with aqueous fluids. This property is obtained only after extensive post foaming operations. These steps include multiple washing in a hydratable salt solution, with each wash followed by nip rolling. The final nip rolling has to be done under vacuum followed by subsequent drying in an air circulating oven. As yet another disadvantage, HIPE foams may exhibit lower stress at user break, percentage elongation at user break, and toughness, especially when wet, than is desirable for certain absorbent uses.

Latex foams used in absorbent applications are likewise known in the art. For example, U.S. Pat. Nos. 3,887,408, 3,901,240, 4,000,028, and 4,069,366 disclose absorbent pads that comprise a laminate having a crushed polymeric latex foam bonded directly to an absorbent layer or bonded to a non-woven layer which is bonded to an absorbent layer. The pad is prepared by forming a foam, drying it without cross-linking, juxtaposing the foam and laminate layer, crushing the foam under pressure to a specified thickness, and then curing the crushed foam. A foam that is cured after crushing would be expected to have a relatively low void volume and therefore a low free absorbent capacity. Moreover, such a foam would not be expected to expand on contact with aqueous fluids or to vertically wick to a high height.

U.S. Pat. No. 4,990,541 teaches combining latex foam with a starch or cellulose based polymer to make an absorbent article. The latex foam is combined with another polymer to obtain the requirement of high absorption of liquids. U.S. Pat. No. 5,763,067 discloses latex foams having saline uptake values of 1.2 and 7.3 grams of saline solution per gram of latex foam, which is too low for use as an absorbent layer.

Wicking, or the ability to draw fluids away from the point of contact, would be advantageous, because it allows for utilization of regions of the absorbent material far from the point of fluid contact. Vertical wicking, that is, drawing fluids in a vertical direction against gravity, would be highly desirable since it allows for more complete utilization of the absorbent product. By moving the fluid away from the point of contact, wicking may also provide a wearer of the absorbent article with a drier feel to the skin. Traditional latex foams do not normally have the ability to wick fluid from the point of contact. While not wishing to be bound by theory, it is believed that poor wicking may be attributable to the relatively large (greater than 50 $\mu$m) cell size found in latex foams.

In view of the above, it would be advantageous to discover a hydrophilic polymeric foam that is capable of acquiring and distributing aqueous fluids, but that is also less complicated to prepare than HIPE foams. It would also be advantageous if the absorbent polymeric foam was inherently hydrophilic, such that post-synthesis functionalization and rinse treatments were not required to achieve hydrophilicity. It would be more advantageous, if the hydrophilic polymeric foam had a high free absorbent capacity. It would be even more advantageous if the hydrophilic polymeric foam was a durable material, as exemplified by good stress at user break, percentage elongation at user break, and toughness, both prior to and after absorbing fluid. Finally, it would be most advantageous if the hydrophilic polymeric foam was capable of vertically wicking aqueous fluids to a high height and rapidly. A polymeric foam composition having all of the aforementioned properties would be highly desirable for use in absorbent applications.

SUMMARY OF THE INVENTION

Surprisingly we have discovered that latex foams can be produced that have fluid capacities greater than about 10 grams of saline solution per gram of foam and can also vertically wick saline solution to a height of greater than about 15 cm without extensive post foaming operations.

In one aspect, this invention is a novel composition comprising a durable, conformable, hydrophilic, polymeric latex foam, which is capable of acquiring and distributing aqueous fluids. The polymeric foam of this invention is further characterized as being capable of vertically wicking a 0.9 weight percent solution of sodium chloride in water (hereinafter, "a 0.9 weight percent aqueous saline solution"), to a height of greater than about 5 centimeters (cm). The term "vertical wicking," as noted hereinbefore, refers to drawing a fluid away from the point of contact in a vertical direction against gravity. For the purposes of this invention, vertical wicking is expressed in units of height (for example, centimeters) and is measured in a manner described in the Test Procedures section, included hereinbelow. In a preferred aspect, the durable, conformable, hydrophilic absorbent latex foam composition of this invention remains thin after compression and prior to wetting without the need for complex operations; but upon wetting, the compressed foam expands as it absorbs fluid. This property of remaining compressed until wetted will be referred to hereinafter as "thin-till-wet."

The novel polymeric foam composition of this invention can be employed as an absorbent in products which are used to acquire and distribute aqueous fluids, for example, and without limitation, diapers, adult incontinence products, feminine hygiene products, wiping toweling and sponges, wound dressings and surgical sponges, clothing apparel, food packaging, cable wrap, and water block tape. Advantageously, the absorbent polymeric foam of this invention is inherently hydrophilic, which eliminates the need for post-synthesis functionalization or rinse treatments to induce hydrophilicity. As yet another advantage, the absorbent polymeric foam of this invention possesses a high free absorbent capacity and possesses good stress at user break, percentage elongation at user break, and toughness, both prior to and after absorbing fluids. Most advantageously, the absorbent polymeric foam of this invention is capable of vertically wicking aqueous fluids to a high height and rapidly.

In a second aspect, this invention is a process of preparing a durable, conformable, hydrophilic, polymeric latex foam composition, which is capable of acquiring and distributing aqueous fluids and which is capable of vertically wicking a 0.9 weight percent aqueous saline solution, to a height of greater than about 5 cm. The process of preparing the aforementioned composition comprises:

(a) frothing a formulation comprising a reactive latex polymer, the formulation being designed to produce a durable, conformable, hydrophilic, polymeric latex foam capable of acquiring and distributing fluids, and capable of vertically wicking a 0.9 weight percent aqueous saline solution to a height of greater than about 5 cm;

(b) drawing the frothed latex formulation into a desired shape;

(c) setting the shaped latex formulation under conditions sufficient to prepare the aforementioned durable, conformable, hydrophilic, polymeric latex foam composition; and (d) optionally, compressing the latex foam under conditions sufficient to prepare a "thin-till-wet" foam composition.

The process of this invention is desirable for preparing durable, absorbent latex foams having a high vertical wicking capacity for aqueous fluids as well as a high free absorbent capacity. As a further advantage, the process of this invention is less complicated than high internal phase emulsion polymerization methods of the prior art. As a further advantage of this invention, the preparation of the novel composition does not require vulcanization, which is often found in latex foam prior art.

In a third aspect, this invention is an article of manufacture selected from the group consisting of diapers, feminine hygiene products, clothing apparel, wiping towels, wiping sponges, wound dressings, surgical sponges, food packaging, cable wraps, and water block tapes, the article comprising the aforementioned durable, absorbent, conformable, hydrophilic, polymeric latex foam composition of this invention.

DETAILED DESCRIPTION OF THIS INVENTION

A novel composition is disclosed herein comprising a durable, conformable, hydrophilic, polymeric latex foam, which is capable of acquiring and distributing aqueous fluids. The term "aqueous fluid" is meant to include essentially pure water, aqueous saline solutions, as well as aqueous solutions containing one or more soluble components selected from inorganic and organic compounds and ions, including, but not limited to bodily fluids (including but not limited to urine, blood or menstrual fluid, perspiration, etc.), water, milk, juice, meat drippings, etc.

The polymeric foam of this invention is further characterized as being capable of vertically wicking a 0.9 weight percent aqueous saline solution, to a height of greater than about 5 cm, preferably, greater than about 10 cm, more preferably greater than about 15 cm, and most preferably, greater than about 20 cm, with vertical wicking being measured for the purposes of this invention in the manner described in the Test Procedures section, included hereinbelow.

For the purposes of this invention, the term "durable" will refer to a desirable level of stress at user break, percentage elongation at user break, and toughness. These three physical properties are known to those skilled in the art of materials science, and more specifically, polymer science. General definitions of the aforementioned physical properties and their methods of measurement can be found in textbooks in the general art, for example, in *Textbook of Polymer Science*, $2^{nd}$ ed., Fred W. Billmeyer, Jr., Wiley-Interscience, John Wiley & Sons, Inc., New York, 1971. Stress at user break, percentage elongation at user break, and toughness are more specifically defined for the purposes of this invention in the Test Procedures section included below. The desirable levels of stress at user break, percentage elongation at user break, and toughness, as applied to the composition of this invention, are also described hereinafter.

For the purposes of this invention, the term "conformable" is defined as having the ability to bend and flex to the desired shape of the user; for example, the shape of a wearer of the absorbent article.

The term "hydrophilic," as used herein, will describe a material or surface of a material that is wettable by aqueous fluids, including aqueous bodily fluids, deposited on these materials. Hydrophilicity and wettability are typically defined in terms of contact angle. Contact angles are measured by placing a drop of fluid on the material or surface, also referred to as a substrate. The "contact angle" is defined as the angle between the substrate and a line tangent to the liquid droplet at the point at which the liquid contacts the substrate. A material or surface of a material is said to be wetted by a fluid (that is, hydrophilic) when either the contact angle between the fluid and the material, or its surface, is less than 90 degrees, or when the fluid tends to spread spontaneously across the surface of the material, both conditions normally co-existing. A contact angle of 0 degrees corresponds to a droplet that completely wets the substrate. Conversely, a material or surface is considered to be hydrophobic if the contact angle is 90 degrees or greater than 90 degrees, and the fluid does not spread spontaneously across the surface of the material. A contact angle of 180 degrees corresponds to an essentially perfectly spherical droplet on the substrate. The subjects of wettability and contact angles are discussed in detail by Milton J. Rosen in *Surfactants and Interfacial Phenomena*, $2^{nd}$ edition, John Wiley & Sons, Inc., 1989.

In preferred embodiments of this invention, the durable, conformable, hydrophilic polymeric foam is still further characterized as having a free absorbent capacity for a 0.9 weight percent aqueous saline solution of greater than 5 grams, preferably about 10 grams, more preferably, greater than about 15 grams, most preferably, greater than about 18 grams of saline solution absorbed per gram of dry foam (gig). The term "dry foam" refers herein to a foam which essentially has not been wetted, except as what wetness may pre-exist in the foam after curing or on standing in the ambient environment. A detailed description of the measurement of free absorbent capacity is given in the Test Procedures section, included hereinbelow.

In another preferred aspect of this invention, the durable, conformable, hydrophilic polymeric latex foam is ionic. As used herein, the term "ionic" will mean that the material contains ionic groups, an ion being any atom or radical that has lost or gained one or more electrons and has thus acquired an electric charge. Both cations (positively charged ions) and anions (negatively charged ions) are suitably included. The ionicity of the composition of this invention may be derived from ionic substituents present on the latex polymer chain, including residual unreacted ionic functionalities, such as carboxylate groups; or alternatively, from ionic substituents on additives present in the polymer formulation, for example, foaming aids, foam stabilizers, pH control agents, and thickeners. Typically, however, inorganic salts, such as calcium chloride, are not present in bulk in the polymer and, therefore, are not the source of ionic charge.

A second aspect of this invention is a process for preparing the durable, conformable, hydrophilic, polymeric latex foam composition, which is capable of acquiring and distributing fluids and which is characterized by high vertical wicking and the aforementioned preferred free absorbent capacity. The process comprises the following steps:

(a) frothing a formulation comprising a reactive latex polymer, the formulation being designed to produce a durable, conformable, hydrophilic, polymeric latex foam capable of acquiring and distributing aqueous fluids, and capable of vertically wicking a 0.9 weight percent aqueous saline solution, to a height of greater than about 5 cm;

(b) drawing the frothed latex formulation into a desired shape;

(c) setting the shaped latex formulation under conditions sufficient to prepare the aforementioned durable, conformable, hydrophilic, polymeric latex foam composition; and (d) optionally, compressing the latex foam under conditions sufficient to prepare a "thin-till-wet" foam composition.

As noted hereinbefore, the phrase "thin-till-wet" means that after compression and prior to wetting, the foam composition remains thin or compressed; but upon wetting the compressed foam expands and becomes thicker. The extent of compression, hence the thickness of the pre-wetted foam, can vary depending on the application. Typically, the thickness of the thin-till-wet foam is less than about 75 percent, more typically less than about 50 percent, still more typically less than about 25 percent of its pre-compressed thickness prior to wetting. The thickness of the thin-till-wet foam can be less than about 10 percent of its pre-compressed thickness prior to wetting. Upon absorbing its full or nearly full capacity of fluid, the foam typically reaches greater than about 50 percent, more typically, greater than about 75 percent, still more typically, greater than about 90 percent of its pre-compressed thickness, in the absence of any constraining forces.

The formulation in step (a), above, comprises a latex polymer having certain reactive functional groups. Preferably, the formulation additionally contains a water-dispersible coreactive material (cross-linking agent) having two or more groups capable of reacting with the reactive functional groups of the latex polymer. By "water-dispersible material" is meant a material that is soluble or dispersible in water or a water miscible liquid. The formulation may also contain other components such as foaming aides, foam stabilizers, pH control agents, thickeners, fillers, antioxidants, gelling agents, plasticizing components, and the like. Frothing or foaming of the formulation can be accomplished by one of several known methods, such as by using blowing agents, by whipping, or by use of any suitable apparatus having commercially available foaming heads.

The reactive latex polymers suitable for use in this invention typically are polymers of one or more ethylenically unsaturated monomers selected from the class of styrene and monomers copolymerizable with styrene, for example, a copolymer comprising a monovinylidene aromatic monomer, an aliphatic conjugated diene monomer, and/or an $\alpha,\beta$-ethylenically unsaturated carboxylic acid.

At least one of such ethylenically unsaturated monomers which is polymerized to form the reactive latex consists of those polymerizable ethylenically unsaturated monomers having at least one type of pendant reactive group, such as carboxy, sulfo, primary amino, secondary amino, amido, methylolamido, sulfonamido, primary hydroxyl, secondary hydroxyl, phenolic hydroxyl, aldehydic, and epoxy groups. Alternatively, the polymerizable ethylenically unsaturated monomer may have substituent groups which, subsequent to polymerization, can be converted to such reactive substituent groups, for example, ester, nitrile, amide, or salt groups which can be hydrolyzed to reactive acid, amine, or hydroxyl groups. Zwitterionic monomers can also be used to make zwitterionic latex polymers, as described in U.S. Pat. No. 6,025,404, incorporated herein by reference.

Non-limiting examples of suitable ethylenically unsaturated monomers having pendant reactive substituent groups include acrylic acid, methacrylic acid, itaconic acid, fumaric acid, maleic acid, ethyl acid maleate, 2-sulfoethyl acrylate, 2-sulfoethyl methacrylate, 2-amino ethyl methacrylate hydrochloride, 2-aminoethyl acrylate hydrochloride, vinyl benzylamine, glycidyl methacrylate, hydroxystyrene, acrolein, methacrolein, allyl alcohol, vinylbenzyl alcohol, 2-hydroxyethyl acrylate, 2-hydroxyethyl methacrylate, acrylamide, bis-N-methylol acrylamide, N-methylolmethacrylamide, N-methylolmethacrylamide, bis-N-methylolmethacrylamide, methacrylamide, N-$\beta$-hydroxyethyl acrylamide, N-$\beta$-hydroxyethyl methacrylamide, $\beta$-hydroxypropyl acrylate, $\beta$-hydroxypropyl methacrylate, $\gamma$-hydroxypropyl methacrylate, 6-hydroxyhexyl acrylate, 6-hydroxyhexyl methacrylate, sodium styrene sulfonate, sodium $\alpha$-methylstyrene sulfonate, 2-methylaminoethyl acrylate hydrochloride, 2-methylaminoethyl methacrylate hydrochloride, 3-methylaminopropyl acrylate hydrochloride, 3-methylaminopropyl methacrylate hydrochloride, 3-methylaminobutyl acrylate hydrochloride, 3-methylaminobutyl methacrylate hydrochloride, 3-ethylaminopropyl acrylate hydrochloride, and styrene sulfonamide.

Among the ethylenically unsaturated monomers of the class of styrene and monomers copolymerizable with styrene are the monomers having one or more reactive substituent groups listed above; the monovinylidene aromatic monomers (the styrene compounds); unsaturated acid derivatives, such as the acrylic esters, acrylic nitriles, maleic esters, and fumaric esters; unsaturated alcohol esters; unsaturated ketones; the conjugated olefins; and other compounds containing one or more ethylenic linkages capable of addition polymerization.

Specific non-limiting examples of such ethylenically unsaturated compounds are styrene, α-methylstyrene, ar-methylstyrene, ar-ethylstyrene, α-ar-dimethylstyrene, ar, ar-dimethylstyrene, ar-t-butylstyrene, vinylnaphthalene, methoxystyrene, cyanostyrene, acetylstyrene, monochlorostyrene, dichlorostyrene, and other halostyrenes, methylmethacrylate, ethyl acrylate, butyl acrylate, hexyl acrylate, 2-ethylhexyl acrylate, lauryl methacrylate, phenyl acrylate, acrylonitrile, methacrylonitrile, ethyl α-chloroacrylate, diethyl maleate, polyglycol maleate, vinyl chloride, vinyl bromide, vinylidene chloride, vinylidene bromide, vinyl methyl ketone, methyl isopropenyl ketone, vinyl ethyl ester, 1,3-butadiene, isoprene, and the like.

Latexes of the above polymers are prepared by polymerizing one or more ethylenically unsaturated monomers of the class of styrene and monomers copolymerizable with styrene, at least one of which contains a pendant substituent reactive group, by conventional emulsion polymerization methods.

In one preferred embodiment, the reactive latex is selected from epoxy modified styrene/butadiene latex polymers, preferably, styrene/butadiene/glycidyl methacrylate latex. In another preferred embodiment, the reactive latex polymer is an ionically-functionalized latex polymer that produces an Tonically functionalized foam; more preferably, an ionically-functionalized styrene/butadiene latex polymer, and even more preferably, a carboxylated styrene/butadiene latex polymer. Most preferably, the reactive latex is a styrene/butadiene/acrylic acid, styrene/butadiene/itaconic acid, or a styrene/butadiene/glycidyl methacrylate latex polymer.

Any reactive latex solids content can be employed in the latex polymer formulation, provided that the composition of this invention is achieved. Generally, the reactive latex solids content of the formulation is greater than about 20 weight percent, preferably, greater than about 30 weight percent, and more preferably, greater than about 40 weight percent, based on the total weight of the formulation. Generally, the reactive latex solids content of the formulation is less than about 80 weight percent, typically, less than about 70 weight percent, and more typically, less than about 60 weight percent, based on the total weight of the formulation.

The coreactive materials or cross-linking agents, which are preferably mixed with the reactive latexes prescribed for this invention, are those materials which are soluble or dispersible in water or in water-miscible liquids and which contain at least one carbon atom and which have at least two substituent groups coreactive with the reactive groups on the copolymer of said latex. There may be selected as the coreactive material for use with the reactive latex component other latexes which contain polymers having a plurality of substituent groups which also are coreactive with the substituent groups on the copolymer of the said reactive latex. Representative coreactive substituent groups are (a) methylol groups when attached to a nitrogen atom, (b) modified methylol groups which have been alkylated with an alcohol having from 1 to 4 carbon atoms when such groups are attached to a nitrogen atom, (c) methylol groups when attached to the aromatic ring of a phenolic compound, (d) carboxyl groups, (e) primary amino groups, (f) secondary amino groups, (g) epoxy groups, and (h) zwitterionic functionalities. The nitrogen atom in (a) and (b) may be a part of the main chain or ring of the compound or polymer. Vulcanization, crosslinking using sulfur, is preferably not employed in this invention.

Non-limiting examples of suitable coreactive materials include melamine, melamine-formaldehyde condensates, urea, urea-formaldehyde condensates, methylated melamine-formaldehyde condensates, methylated urea-formaldehyde condensates, butylated melamine-formaldehyde condensates, butylated urea-formaldehyde condensates, phenol-formaldehyde condensates, ammonia-formaldehyde-hydrochloric acid condensates, liquid epoxy resins, ethylene diamine-formaldehyde condensate, hexamethylene diamine-formaldehyde condensate, polyethyleneimine, ethylene diamine, diethylenetriamine, triethylene tetramine acetate, trimethylene diamine, tetramethylene diamine, hexamethylene diamine, decamethylene diamine, tetraethylene pentamine, guanidine, formoguanamine, benzoguanamine, dicyandiamide, malonic acid, succinic acid, glutaric acid, adipic acid, pimelic acid, suberic acid, azaleic acid, sebacic acid, polyacylic acid, a latex comprising a copolymer of styrene, 1,3-butadiene and 2-aminoethylmethacrylate hydrochloride, and a latex comprising vinyl chloride, vinylidene chloride, 2-sulfoethyl methacrylate, ethylene glycol diglycidyl ether, polyethylene glycol diglycidyl ether, diethylene glycol diglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, propylene glycol diglycidyl ether, polypropylene glycol diglycidyl ether, resorcinol diglycidyl ether, glycidyl ester ether of p-hydroxy benzoic acid, neopentyl glycol diglycidyl ether, 1,6-hexanediol diglycidyl ether, o-phthalic acid diglycidyl ester, and high molecular weight dicarboxylic acid diglycidyl ester. Preferred coreactive materials include ethylene glycol diglycidyl ether, polyethylene glycol diglycidyl ether, diethylene glycol diglycidyl ether, sorbitol polyglycidyl ether, polyglycerol polyglycidyl ether, pentaerythritol polyglycidyl ether, diglycerol polyglycidyl ether, glycerol polyglycidyl ether, trimethylolpropane polyglycidyl ether, propylene glycol diglycidyl ether, polypropylene glycol diglycidyl ether, resorcinol diglycidyl ether, glycidyl ester ether of p-hydroxy benzoic acid, neopentyl glycol diglycidyl ether, 1,6-hexanediol diglycidyl ether, o-phthalic acid diglycidyl ester, and high molecular weight dicarboxylic acid diglycidyl ester. More preferred coreactive materials include epoxy-substituted polyalkylene polyethers. Most preferred coreactive materials include ethylene glycol diglycidyl ether, polyethylene glycol diglycidyl ether, diethylene glycol diglycidyl ether.

If the coreactive material is water-soluble, it may simply be mixed with the latex or the material may be added as an aqueous solution or as a solution in a water-miscible solvent. If the coreactive material is not appreciably soluble in water or a water-miscible liquid, then it is added as an aqueous dispersion. However, any emulsifiers used for the preparation of such dispersions, as well as the emulsifiers used in the manufacture of the latex, preferably are selected so that they are compatible with one another and with the reactive groups on the latex polymer and with the reactive groups on the coreactive material.

If used, the coreactive material can be present in the latex formulation in any amount ranging from greater than about 0 to about 100 parts coreactive material per one hundred parts solids or more, based on the weight of reactive latex solids. If a coreactive material is used, preferably, the coreactive material is present in an amount greater than about 0, more preferably, greater than about 3 parts per one hundred parts solids, based on the weight of the reactive latex solids. If a coreactive material is used, preferably, the coreactive material is present in an amount less than about 20 parts, more preferably, less than about 10 parts, and most preferably, less than about 8 parts per one hundred parts solids, based on the weight of the reactive latex solids.

Foaming aides, foam stabilizers, pH control agents, thickeners, fillers, antioxidants, gelling agents, plasticizing components, and the like, may be included as optional additional components in the formulation. A material will often serve more than one of the aforementioned functions, as may be evident to one skilled in the art, even though the material may be primarily discussed only under one functional heading hereinbelow.

Optionally, foaming aides can be included in the formulation. Foaming aides encourage the formation of foams and froths and include materials such as sodium lauryl sulfate, sodium dodecyl sulfate, and mixtures thereof. If used, foaming aides will be included at levels greater than about 0 parts per one hundred parts solids, based on the weight of the reactive latex solids. If used, foaming aids may be included at levels less than about 50, preferably, less than about 10, and more preferably, less than about 5 parts per one hundred parts solids, based on the weight of the reactive latex solids.

As another option, foam stabilizers can be included in the formulation. Foam stabilizers tend to enhance the integrity of the froth/foam in the shaping and setting process and can also act as foaming aids. Foam stabilizers include, for example, potassium oleate, disodium N-octyldecylsulfosuccinimate, and mixtures thereof. A preferred foam stabilizer is disodium N-octyldecylsulfosuccinimate. If used, the stabilizer will be included at a level greater than about 0 parts per one hundred parts solids, based on the weight of the reactive latex solids. Generally, the stabilizer may be included at a level less than about 50, preferably, less than about 20, more preferably, less than about 10, and most preferably, less than about 5 parts per one hundred parts solids, based on the weight of the reactive latex solids.

Optionally, pH control agents can be included in the formulation. The inclusion of pH control agents can serve both to control the rate of reaction between the reactive latex and coreactive material and to modify the viscosity of the formulation. An adjustment of the pH of the formulation can be made, if desired, by the addition of usual acidifying or alkalizing agents such as acetic acid, citric acid, dilute mineral acids (for example, HCl, $H_2SO_4$, $HNO_3$), ammonium hydroxide, dilute aqueous solutions of alkali metal hydroxides, and the like. If the formulation is not at the desired pH level, the pH usually is adjusted to a value greater than about 7, preferably greater than about 8, and less than about 13, preferably less than about 11, more preferably less than about 10.

As yet another option, thickeners may be included to modify the viscosity of the formulation. Suitable non-limiting examples of thickeners include methyl cellulose, ethyl cellulose, alkali swellable latexes, and alkali soluble latexes. Thickeners may function in multiple roles depending upon the thickener employed; for example, some thickeners may provide hydrophilicity and/or tackifying properties to the polymer. The quantity of thickener that is used will depend upon the thickening efficiency of the specific thickener employed as well as the desired end viscosity. One skilled in the art would know how to determine the amount of specific thickener needed to achieve the desired viscosity. Typically, the amount of thickener used ranges from greater than about 0 to less than about 20 parts per one hundred parts solids, based on the weight of the reactive latex solids.

Optionally, one or more fillers can also be included in the formulation to modify the solids or foam's physical and/or visual properties. Optional fillers include, for example, talc, calcium carbonate, titanium dioxide, carbon black, redispersible latex, plastic pigments, fumed silica, hollow ceramic microspheres, and hollow glass microspheres. Rigid fillers can be used to increase the stiffness of the final foam, while flexible fillers can be used to decrease the stiffness of the final foam. Low density fillers, such as hollow ceramic microspheres and hollow glass microspheres, can be used to decrease the density of the final foam, thereby increasing the g/g fluid capacity of the foam without the need to froth to a higher void volume. When employed, the filler will typically be provided in an amount greater than about 1 to less than about 100 parts per 100 parts solids, based on the weight of the reactive latex solids.

Optionally, antioxidants may also be included in the formulation. Antioxidants inhibit oxidation of the froth/foam during the setting process. Oxidation can discolor the foam and degrade its final physical properties. Antioxidants are well known in the art. Examples of antioxidants include, but are not limited to, substituted phenolic compounds such as butylated dihydroxyanisole, di-tert-butyl-p-cresol, and propyl gallate. Additional examples of antioxidants include aromatic amines, such as, di-beta-naphthyl-para-phenylenediamine and phenyl-beta-naphthylamine. Two commercially available compositions of antioxidants include Aquamix™ 494 (Harwick Chemical Corporation) brand and Lowinox® Emulsion L (Chemische Werke Lowi GmbH & Company) brand antioxidants. Aquamix™ 494 brand antioxidant is a composition comprising the diester of 3-(dodecylthio) proprionic acid, tetraethylene glycol, and the reaction products of 4-methylphenol with dicyclopentadiene and with isobutylene. If used, the antioxidants may be included in the formulation at a concentration of greater than about 0 parts per one hundred parts solids, based on the weight of the reactive latex solids. If used, the antioxidants may be included in the formulation at a concentration of less than about 10, preferably, less than about 5, more preferably, less than about 2 parts per one hundred parts solids, based on the weight of the reactive latex solids.

Optionally, gelling agents may be included in the formulation to facilitate the gelling of the semi-liquid viscous foam to form a solid cellular structure upon drying and curing. The mechanism of gelling should be carefully monitored and controlled. Gelation of the foam can result from the hydrolysis of relatively insoluble acid forming chemicals such as the ammonium, sodium or potassium salts of silicofluorides. Gelation of the foam can also result from the decomposition of suitable heat sensitive ammonium salts such as the ammonium sulfates, nitrates, chlorides, thiocyanates, formates and acetates. The incorporation of hydrolyzable electrolytes or heat sensitive ammonium salts can be accomplished after compounding and frothing of the liquid foam. Typically, the gellants are carefully metered into the froth after foaming, but before drawing the froth into the desired shape. Gelling agents, such as those disclosed in U.S. Pat. No. 4,205,103 (incorporated herein by reference), may also be incorporated into the foam latex or finished foam compound prior to frothing. The quantity of gelling agent employed will be selected based upon the gelling capacity of the selected gelling agent as well as the targeted viscosity to be achieved.

Optionally, plasticizing components may be included in the formulation to reduce the effective glass transition temperature (Tg) of the latex foam composition of this invention. The effective Tg is the temperature at which the foam transforms from rigid (non-conformable) to flexible (conformable). Plasticizers include any additive that increases the flexibility of the polymer. Plasticizers include surfactants with long chain hydrophobic ends, oils, solvents, and the like. The quantity of plasticizer employed will be selected based upon the desired foam flexibility.

The formulation is designed so as to produce a conformable foam after forming and setting. One skilled in the art can design the formulation in many ways so as to produce the conformable foam; but generally conformability is controlled by the effective Tg of the foam. Hence, the effective Tg of the foam composition of this invention preferably lies below the temperature at which the material is designed to be used. Preferably, the effective Tg of the foam composition of this invention is below about 40° Centigrade (C), more preferably, below about ambient temperature (taken as about 25° C.), still more preferably, below about 10° C. The effective Tg can be determined, for example, by standard Theological methods used in the art, such as, compression modulus. The effective Tg can be adjusted, for example, by the choice of reactive latex, optional coreactive material (or cross-linking agent), and optional plasticizing components. Accordingly, the effective Tg of the final foam composition may be different from the Tg of the neat latex polymer.

The formulation of reactive latex and any optional components may be foamed or frothed by blowing agents and methods of their use which are applicable to the known latex foam art. One method involves releasing a gas, such as nitrogen or air, into the formulation. Other suitable gases include, for example, carbon dioxide, helium, argon, and freons. Another method involves chemically reacting a gas-liberating material with an ingredient in the formulation, with the consequential liberation of a gas as a reaction product. The mixture of the reactive latex and optional components can also be foamed by whipping or by use of any apparatus having commercially available foam heads. Typically, the volume of the frothed formulation is increased more than about 5 times, preferably, more than about 10 times, more preferably, more than about 15 times, and most preferably, more than about 20 times, as compared with the original volume of the formulation before frothing. Typically, the volume of the frothed formulation is less than about 50 times that of the original volume.

Typically, a foam density is targeted which would yield a free absorbent capacity in the finished latex foam composition, in the absence of filler, of greater than 5 grams 0.9 weight percent saline solution per gram latex foam. Preferably, a foam density is targeted which would yield a free absorbent capacity, in the absence of filler, of greater than about 10 g/g, even more preferably, greater than about 15 g/g, and most preferably, greater than about 18 g/g. At a given void volume, the g/g free absorbent capacity can be increased by incorporating into the foam a low density filler material that decreases the foam density, for example, hollow ceramic or glass microspheres. Suitable foam densities, prior to compression and in the absence of filler, are generally greater than about 0.02 grams per cubic centimeter (g/cm³). Generally, prior to compression and in the absence of filler the foam density is less than about 0.20 g/cm³. Preferably, the foam density prior to compression and in the absence of filler is less than about 0.10 g/cm³, more preferably, less than about 0.07 g/cm³, and more preferably, less than about 0.05 g/cm³.

The frothed formulation is then shaped by any method known in the art, such as, one or more of the following: (a) pouring or spreading into molds, (b) spreading on a flat tray or belt, (c) coating or laminating onto substrates, or by (d) layering or blending two or more froths. For the purpose of this invention, the term "substrate" is defined as any material, such as, a collection of fibers, cloth, fabric, synthetic nonwoven material, polymer film, non-latex polymer foam, including polypropylene and urethane foams, leather, wood, glass, metal, or any other form of backing to which the frothed mixture will adhere when applied and after it is cured. Where suitable, the substrate and/or the latex foam can be punctured with a collection of microapertures before or after curing to assist in wicking fluid. In a preferred example, the absorbent latex foam of this invention can be laminated onto a microapertured non-woven fabric. This design is desirable in the diaper and feminine hygiene care products area, because the non-woven fabric gives a softer feel to the skin, while the microapertures improve wicking resulting in a feeling of dryness.

Another preferred shaping process includes coating the froth onto a substrate that has superabsorbent polymer either incorporated in or layered on the substrate, the term "substrate" being distinct from the latex foam and as defined hereinabove. For example, the substrate can have superabsorbent fibers or powder incorporated into the substrate itself; the substrate can have a superabsorbent film on the substrate surface being coated, either uniformly coated or patterned; the substrate can have superabsorbent polymer in the form of fibers or granules randomly distributed or specifically patterned on the surface of the substrate being coated. The superabsorbent can advantageously be included in a pattern in or on the substrate, such that in diaper applications fluid is absorbed in superabsorbent polymer in desired targeted locations in the diaper. The advantage of this aspect of the invention is that the superabsorbent components are essentially not free to redistribute in the article, in contrast to conventional diapers where superabsorbent granules are distributed into cellulose fluff. Other advantages of including patterned superabsorbent polymer in or on the substrate being coated are that (1) fluid can be stored in targeted locations of an article, such as a diaper, and (2) designs, logos, pictures, etc. can be patterned into and/or onto the substrate such that when the article is wet the design, logo, picture, etc. will swell and become apparent.

As another processing option, two or more froths can be combined during the shaping process to form layered or blended froths. For example, a first froth can be prepared so as to achieve a foam with large cell diameters, while a second froth can be prepared so as to achieve a foam with small cell diameters. The first froth can be shaped as previously described, and the second froth can then be shaped on top of the first froth, either before or after setting. Large and small cell diameters are specified hereinafter. In addition to layering, two or more froths can be swirled or blended together just prior to shaping in an effort to shape froths with zones of different properties. For example, the first and second froth described in the layered froth example can be swirled together prior to or during shaping, producing a foam after setting that has swirled zones of large and small cell sizes. Likewise, optionally, a substrate and/or a discrete layer of superabsorbent can be positioned between layers of froth, if desired.

Preferably, the shaping is done on a continuously moving belt such that the shaped froth is moved directly to the setting process. A continuous moving belt process can include, for example, a doctoring bar that levels the top of the froth to the desired thickness. Additionally, the sides of the belt can be shaped in such a way as to define the shape of the foam for a final product. For example, the belt can be shaped in such as way as to produce a roll-stock of foam comprising continuous "hourglass" type sections that can be cut at unit intervals for diaper inserts. By shaping the sides of the froth in this manner one reduces the waste foam that would be produced, if the hourglass shape were cut from a rectangular shaped section.

The shaped froth is set and dried, typically by heating for a period of time sufficient to form a substantially dry polymeric foam structure. Setting and drying processes are well known in the art of latex froth foams and are dependent upon the type of reactive latex used; what, if any, coreactive material is used; and what, if any, gelling agents are used. Setting and drying is typically done at temperatures greater than about 90° C. and less than about 200° C. for anywhere from less than 1 min to about 90 min. Thicker foams often take longer to set and dry at a given temperature than do thinner foams. Denser foams tend to take longer to set and dry at a given temperature than do lower density foams.

The foams of this invention are also characterized by an open-cell structure and, prior to compression, a cell size typically ranging from greater than about 50 microns ($\mu$m) to less than about 2 mm in diameter (or cross-sectional dimension), as determined by scanning electron microscopy (SEM).

The polymeric walls, or struts, in the foams of the present invention are typically characterized by having distinct domains derived from the surface materials of the latex particles (typically carboxylate rich material). For example, films of carboxylated latexes prepared at higher pH (above about 7) are known to have girder-like networks of carboxylated material throughout the latex film, outlining what used to be the surface of the individual latex particles. Alternatively, the films of carboxylated latexes prepared at lower pH (about 3) are known to produce carboxylated material highly dispersed as discrete particles throughout the latex film. These two types of domains have been well established, for example, by C. S. Kan and J. H. Blackson in "Effect of Ionomeric Behavior on the Viscoelastic Properties and Morphology of Carboxylated Latex Films," *Macromolecules*, 29 (1996), 6853–6864. These types of domains in the cell wall are believed to contribute to the durability of the latex foam and are not expected for foams prepared directly from monomers, such as polymerized HIPE foams, since HIPE foams do not originate from particles.

Without being bound by theory, it is believed that the domains, described hereinabove, distributed throughout the latex walls or struts, contribute to the durability of the latex foam by reinforcing the polymer. The carboxylated-latex formulations utilized in preparing the foams of this invention typically have a pH above 7, so they are expected to have a substantially honeycomb structure of carboxylate-rich material within their polymer walls. Indeed, transmission electron microscopy (TEM) analysis of the foam from Example 2, hereinbelow, reveals the expected honeycomb structure. Crosslinking of the latex typically occurs with the surface functionality, typically carboxylate functionality, on the latex particle. Therefore, the resulting honeycomb network would be expected to correspond to a largely continuous film knitting the individual latex particles together by crosslinks, thereby establishing a reinforcing structure throughout the polymer wall or strut. Similarly, if highly dispersed domains are established they would be expected to correspond to zones of higher crosslinking, which could hinder the progression of a tear or fracture through the polymer wall.

Formulations that blend latexes of higher Tg and lower Tg may also create foams with different types of advantageous structure in the polymer walls or struts. One can choose a lower Tg latex to ultimately form the continuous structure of the wall or strut, while the higher Tg latex remains primarily a particle in the wall or strut, yet crosslinked to the film of the lower Tg latex. In such a situation, the higher Tg latex acts essentially as a crosslinking filler, reinforcing the polymer wall or strut.

One preferred embodiment of this invention involves shaping a relatively thick foam and then setting and drying it sufficiently slowly such that the cells in the center of the foam are relatively large and gradually get smaller towards the surfaces of the foam. The gradient structure is the result of a relatively quick set of the surface of the froth as compared to the interior of the froth. As a result, the interior of the froth is allowed to coarsen after the surface structure has already been set. Optionally, the resulting foam can be sliced, for example, roughly in half, that is, about midway between the two surfaces perpendicular to the thickness axis, producing two foams having a gradient of cell sizes, large on one surface and small on the opposing surface. Another method of obtaining a cell size gradient involves curing one side of the foam at a cooler temperature than the opposing side of the foam. Foams with such a gradient structure are particularly useful in rapidly acquiring fluids and solid particulates on the surface having the large cell sizes, while rapidly wicking the fluid away from the point of acquisition through the small cells near the opposing surface. For the purposes of this invention, a small cell will typically range in size from about 50 microns ($\mu$m) to about 150 $\mu$m, and a large cell will typically range in size from greater than about 150 $\mu$m to about 2 millimeters (mm).

The foams of this invention are inherently hydrophilic requiring no post modification. The hydrophilicity may be provided by the latex polymer itself, for example, if hydrophilic functional groups, such as hydroxyls or carboxylic acids, are present in the polymer. Additionally or alternatively, hydrophilicity may be provided by hydrophilic components in the latex formulation, such as, hydrophilic foaming aids, froth stabilizers, thickeners, and the like.

As noted hereinbefore, the composition of this invention is capable of vertically wicking a 0.9 weight percent aqueous saline solution to a height of typically greater than about 5 cm, preferably, greater than about 10 cm, more preferably, greater than about 15 cm, and most preferably, greater than about 20 cm. Generally, the composition of this invention wicks aqueous fluids rapidly; for example, vertical wicking of a 0.9 weight percent aqueous saline solution to a height of typically greater than about 5 cm, preferably greater than about 7 cm, and more preferably, greater than about 10 cm in 2 min is typically achieved.

Durability, as measured by stress at user break, percentage elongation at user break, and toughness, is also useful in characterizing the latex foam composition of this invention. Prior to being wetted, the latex foams of the present invention typically have a durability characterized by having: (1) a stress at user break of typically greater than about 50 pounds per square inch (psi), preferably, greater than about 75 psi, and more preferably, greater than about 100 psi; (2) elongation at user break of typically greater than about 100 percent, preferably, greater than about 150 percent, more preferably, greater than about 200 percent, even more preferably, greater than about 250 percent, and most preferably, greater than about 280 percent; and (3) a toughness of typically greater than about 100 psi, preferably greater than about 150 psi, and more preferably greater than about 200 psi.

At essentially full absorbent capacity with a 0.9 weight percent aqueous saline solution, the latex foams of the present invention have a durability characterized by having: (1) a stress at user break of typically greater than about 5 psi, preferably, greater than about 10 psi, more preferably, greater than about 15 psi, and most preferably, greater than about 20 psi; (2) elongation at user break of typically greater than about 25 percent, preferably, greater than about 50 percent, more preferably, greater than about 100 percent, even more preferably, greater than about 150 percent, still more preferably, greater than about 200 percent, and most preferably, greater than about 250 percent; and (3) a toughness of typically greater than about 1 psi, preferably, greater than about 10 psi, more preferably, greater than about 15 psi, still more preferably, greater than about 20 psi, and most preferably, greater than about 25 psi.

The setting and drying step is optionally followed by a compression step to reduce the thickness of the foam. Compression of the foam can be accomplished by a continuous or batch method. Preferably, the compression is done continuously by running the foam through one or more nip rollers. Compression can also be accomplished, for example, in a hydraulic press. Any pressure can be employed which results in the desired foam thickness. Typically, the pressure is greater than about 28 pounds per square inch gauge (psig) (193 kPa), and preferably, greater than about 70 psig (483 kPa). Typically, the pressure is less than about 700 psig (4,826 kPa), preferably, less than about 210 psig (1,448 kPa). Typically, the compression is conducted at about ambient temperature (taken for this purpose at about 22° C.), but compression at other temperatures is also possible and may be preferred to achieve optimal tacking of the foam into a thin-till-wet configuration.

In another embodiment of this invention, the foam can be microapertured during or after the compression step. Microapertures assist in moving fluid faster through the foam and are particularly helpful at the surface of the foam, if a skin has formed during the curing stage. The foam can be microapertured, for example, by perforating one or both surfaces using one or more nip rollers having needles patterned on their surface(s).

In another embodiment of this invention, the foam can be embossed in the compression step with a design or logo for the purpose of creating a design, or to obtain a more fabric-like feel, or to aid in fluid management.

Preferably, once the foam is compressed it remains in a compressed state without the need for external constraining forces. More preferably, the foam will remain compressed only until wetted, whereupon the foam will expand as it absorbs the fluid ("thin-till-wet"). The compressed foam takes up less space than an expanded foam, which can be an important feature in articles such as diapers where thinner articles are both more comfortable to wear and require less space during shipping and storage. Surprisingly, compressing the foam increases the vertical wicking height for a fluid dramatically. It is believed, but the invention should not be bound to such a theory, that smaller cell sizes produce higher wicking than do larger cell sizes, in the same way, for example, that smaller diameter capillaries produce a higher capillary suction on wicking fluids than do larger capillaries. The "thin-till-wet" foam has the further advantage that the viscous drag component that resists rapid wicking of the fluid is reduced as the foam expands, yet the small cell sizes at the fluid front still induce a high capillary suction that draws the fluid up the foam.

Foams that remain thin when compressed may require a tackifying component to resist the resilient force of the polymeric struts of the foam. The resilient force of the foam struts, acting to re-expand the compressed foam, must be overcome by a "tackifying force" acting to hold the cell walls together. The tackifying force can be achieved any of a number of ways. A foam that is compressed, for example, at a temperature above the effective Tg of the foam can remain compressed as a result of entanglement of the polymer chains. Care should be taken in this method to tack the foam into a compressed state, but not to permanently adhere the walls together. In an alternative method, or simultaneously with the polymer entanglement method, tackifying agents that adhere the cell walls together when the foam is compressed can be included in the formulation. Many materials can act as tackifying agents, including, for example, the thickener components listed hereinabove, the froth stabilizing components listed hereinabove, as well as viscous hydrophobic materials such as polyacrylic acid, partially or fully neutralized polyacrylic acid such as sodium polyacrylate; and glycol, polyglycols, glycerine, sugars, surfactants, and the like. Preferably, the tackifying force is relieved sufficiently when wetted to allow at least partial re-expansion of the foam. The quantity of tackifying agent will depend significantly upon the other components in the formulation. Typically one or more components already discussed sufficiently act as a tackifier and no additional tackifying agent, per se, is required. One skilled in the art can quickly determine the amount of tackifier needed, if any.

Test Procedures

Unless otherwise expressly indicated, the following test procedures are employed in the present patent application. Vertical Wicking Height is determined using a sample strip of foam approximately 1 inch (2.54 cm) wide and approximately 30 cm long. The sample strip is adhered to a plastic plate using double-sided tape and positioned adjacent to a ruler such that the bottom of the sample strip is aligned with the bottom of the ruler. The plate is suspended over a bath of 0.9 weight percent (%) aqueous saline solution with a minimal amount of blue food coloring (to assist in visualizing the fluid front). At "time zero", the bath is raised to just contact the bottom of the foam. The fluid height on the front surface of the foam is recorded at specified time intervals (generally 2, 10, 30 and 60 min).

Free Absorbent Capacity is determined using the sample strip from the vertical wicking measurement. The sample strip is placed in a bath of 0.9 weight percent aqueous saline solution. Once the foam is fully saturated it is removed from the bath with a spatula and placed on a coarse wire mesh where any excess fluid is allowed to drain off. The saturated foam is then weighed to get a wet weight. Once weighed, the sample strip is dried in a forced air oven at 60° C. and then weighed again to get a dry weight. The free absorbent capacity is calculated by dividing the difference between the wet and dry weights by the dry weight of the foam.

Stress at User Break, Percent Elongation (Strain) at User Break, and Toughness (Strain Energy) are all measured using an Instron 55R4201 utilizing a 100-pound (45.3 kg) load cell and a separation rate of 20 inches/minute (50.8 cm/min). Measurements are taken using foam samples 4 inches (10.16 cm) long and 1 inch (2.54 cm) wide. Dry samples are 0.024 inch (0.6 mm) thick; wet samples are approximately 0.23 inch (5.8 mm) thick.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

EXAMPLE 1

A latex formulation was prepared according to Table 1. The brand latexes used (The Dow Chemical Company DL532 and DL313 brand latexes) were based on carboxylated styrene/butadiene monomer. Brand DL532 latex (−37° C. Tg) had the following monomer composition: 60 percent butadiene, 37 percent styrene, and 3 percent acrylic acid. Brand DL313 latex (2° C. Tg) had the following monomer composition: 58 percent styrene, 39 percent butadiene, 3 percent itaconic acid. The latex formulation for this invention was prepared by adding the components in the order listed in Table 1 to a beaker while mixing with a Cowles-type blade. Care was taken to minimize the amount of air entrained.

TABLE 1

Latex Froth Formulation for Example 1

| Component[a] | Name | % Solids | Dry Parts By weight | Wet Parts by weight |
|---|---|---|---|---|
| Latex | DL532 | 51 | 65 | 126.95 |
| Latex | DL313 | 49 | 35 | 71.14 |
| Antioxidant | Aquamix ™ 494 | 58 | 1.50 | 2.59 |
| Froth Stabilizer | Stanfax ™ 318 | 35 | 3.50 | 10.00 |
| Thickener | Methocel ™ E4M | 2.5 | 0.33 | 13.20 |
| Base | NH₄OH | 28 | — (to pH 9) | — (to pH 9) |
| Coreactive material: Epoxy | Ethylene Glycol-Diglycidyl Ether | 100 | 6.00 | 6.00 |

[a]DL532 and DL313 brand latexes and Methocel ™ E4M brand thickener were obtained from The Dow Chemical Company. Aquamix ™ 494 brand antioxidant was obtained from Harwick Chemical Corporation. Stanfax ™ 318 brand froth stabilizer was obtained from Standard Adhesive & Chemical Company, Inc. Ethylene glycol diglycidyl ether (EGDGE) was obtained from Nagase Chemical Ltd. as Denacol ™ EX-810 brand EGDGE.

The latex formulation of Table 1 was frothed using a Kitchen-Aid Mixer (Professional Model) to give a cup weight of 8.6 g. The cup weight corresponds to the weight of froth in a level 3 ounce cup (88.7 cm³). The froth was spread on silicon treated release paper (10 inch×14 inch (25.4 cm×35.56 cm)) and drawn down to a height of 0.5 inches (1.27 cm).

The assembly was fed through an infrared oven (Holman Minimeyor™ Model 214) on a chain-link conveyor belt. The assembly was pulled through the infrared oven by inserting pins through the release paper, which engage the chain-link conveyor. A drawdown bar was supported above the mesh at a spacing corresponding to the desired drawdown thickness. A head of latex froth was maintained against the drawdown bar.

The infrared oven had heaters above and below the conveyor. The top and bottom heaters were set at approximately 100° C. The conveyor speed was set to allow a 30-second dwell time in the oven. After passing through the infrared oven, the froth was placed in a forced air oven at 150° C. for 20 min to yield an uncompressed foam. The foam was cooled to room temperature and then compressed under a pressure of 140 psig (965 kPa) using a hydraulic press. The compressed foam remained thin-till-wet.

Within 24 hours of compressing the foam, the vertical wicking height and free absorbent capacity of the uncompressed and compressed foam were measured, as described in the Test Procedures section hereinabove. Results are set forth in Table 2.

TABLE 2

Wicking Height (cm)

| Time (minutes) | Unpressed | Pressed |
|---|---|---|
| 2.0 | 2.8 | 7.0 |
| 10 | 4.0 | 13.7 |
| 30 | 4.5 | 17 |
| 60 | 4.9 | 18 |
| Free Absorbent Capacity | 17.1 g/g | 17.8 g/g |

Surprisingly, in the optional, preferred embodiment of the invention, compressing these foams gives a significant improvement in wicking properties without loss of fluid capacity.

EXAMPLE 2

A latex formulation was prepared according to Table 1. The brand latexes used (The Dow Chemical Company DL595 and DL313 brand latexes) were based on carboxylated styrenelbutadiene monomer. Brand DL595 latex (−37° C. Tg) had the following monomer composition: 60 percent butadiene, 37 percent styrene, and 3 percent acrylic acid. Brand DL313 latex had a Tg of 2° C. The latex formulation for this invention was prepared by adding the components in the order listed in Table 3 to a beaker while mixing with a Cowles-type blade. Care was taken to minimize the amount of air entrained.

TABLE 3

Latex Froth Formulation for Example 2 and 3

| Component[a] | Name | % Solids | Dry Parts By weight | Wet Parts by weight |
|---|---|---|---|---|
| Latex | DL595 | 51 | 65 | 126.95 |
| Latex | DL313 | 49 | 35 | 71.14 |
| Antioxidant | Aquamix ™ 494 | 58 | 1.50 | 2.59 |
| Froth Stabilizer | Stanfax ™ 318 | 35 | 3.50 | 10.00 |
| Thickener | Methocel ™ E4M | 2.5 | 0.33 | 13.20 |
| Base | NH₄OH | 28 | — (to pH 9) | — (to pH 9) |
| Coreactive material: Epoxy | Ethylene Glycol-Diglycidyl Ether | 100 | 6.00 | 6.00 |

[a]DL595 and DL313 brand latexes and Methocel ™ E4M brand thickener were obtained from The Dow Chemical Company. Aquamix ™ 494 brand antioxidant was obtained from Harwick Chemical Corporation. Stanfax ™ 318 brand froth stabilizer was obtained from Standard Adhesive & Chemical Company, Inc. Ethylene glycol diglycidyl ether (EGDGE) was obtained from Nagase Chemical Ltd. as Denacol ™ EX-810 brand EGDGE.

The latex formulation was frothed using a Cowie-Riding (CR-twin) foamer and using only the first of two mixing heads. The formulation pump was maintained at 10 revolutions per minute (RPM), and the mixing head was maintained at 650 RPM. The air pressure was adjusted to obtain a 8.7–9.0 g cup weight. The cup weight corresponded to the weight of froth in a level 3 once (88.7 cm³) cup. Cup weights were measured before and after drawing down the foam to ensure stability in the froth density. The froth expelled from the mixing head through a 53 inch (134.6 cm) long Tygon™ tube (¼ inch ID (6.3 mm ID)).

The froth was drawn down to a thickness of 0.25 inch (6.3 mm) onto a 10-inch (25.4 cm) by 14-inch (35.6 cm)

Teflon™-coated mesh that had approximately 1-mm wide fibers with approximately 1-mm wide spaces between fibers. The mesh was fed through an infrared oven (Holman Minimeyor™ Model 214) on a chain-link conveyor belt. The mesh was pulled through the infrared oven by inserting pins through the mesh, which engage the chain-link conveyor. A drawdown bar was supported above the mesh at a spacing corresponding to the desired drawdown thickness. A head of latex froth was maintained against the drawdown bar.

The infrared oven had heaters above and below the conveyor. The top and bottom heaters were set at approximately 100° C. The conveyor speed was set to allow a 30-second dwell time in the oven. After passing through the infrared oven, the froth was placed in a forced air oven at 150° C. for 20 min to yield an uncompressed foam. The foam was cooled to room temperature and then compressed under a pressure of 140 psig (965 kPa) using a hydraulic press. The compressed foam remained thin-till-wet.

Within 24 hours of compressing the foam, the vertical wicking height and free absorbent capacity of the compressed foam were measured, as described in the Test Procedures section hereinabove. Results are set forth in Table 4.

TABLE 4

Free Absorbent Capacity and Vertical Wicking Results

| Time (minutes) | Unpressed/Pressed 2[a] | Unpressed/Pressed 3[b] |
|---|---|---|
| 2.0 | 5.8/8.0 | 6.4/7.1 |
| 10 | — | 9.9/19 |
| 30 | 11.6/24.5 | 11.1/>25 |
| 60 | 14.1/26.6 | 11.6/>25 |
| Free Absorbent Capacity | 18 g/g | 15 g/g |

[a]Foam drawdown = 0.25 inch (6.3 mm).
[b]Foam drawdown = 0.5 inch (12.5 mm).

Compressing these foams gives a significant improvement in wicking properties if desired without loss of fluid capacity.

It was found, as evidenced in Examples 2 and 3 hereinabove, that the latex foam composition of this invention was capable of vertically wicking a 0.9 weight percent aqueous saline solution to a height greater than 20 cm. The wicking height of the latex foam composition was observed to be greater than 5 cm in 2 min, and in a preferred embodiment equal to 10 cm in 2 min. Additionally, the latex foam composition of this invention was found to have a free absorbent capacity of greater than 15 g aqueous saline solution per g foam.

EXAMPLE 3

A foam was prepared and tested as in Example 2, with the exception that the thickness of the foam strip for the vertical wicking test and the free absorbent capacity test was 0.5 inch (12.5 mm) rather than 0.25 inch (6.3 mm). After compression, the foam remained thin-till-wet. Vertical wicking and free absorbent capacity tests were run within 24 hours of compressing the foam and in the manner described in the Test Procedures above. Results are shown in Table 4.

In addition, a comparison of the data of Tables 2 and 4 illustrates the advantages of using a commercial foamer. In particular, for examples, foams prepared with the commercial foamer demonstrated 30 minute wicking heights which were double those realized using the lab scale Kitchen Aid Mixer.

EXAMPLE 4

A latex formulation was prepared according to Table 5. The formulation was prepared by adding the components to a beaker in the order listed while mixing with a Cowles-type blade. Care was taken to minimize the amount of air entrained.

TABLE 5

Latex Froth Formulation for Example 4

| Component[a] | Name | Percent Solids | Dry Parts by weight | Wet Parts by weight |
|---|---|---|---|---|
| Latex | DL595 | 51 | 65 | 126.95 |
| Latex | DL313 | 49 | 35 | 71.14 |
| Anti-oxidant | Aquamix ™ 494 | 58 | 1.50 | 2.59 |
| Froth Stabilizer | Stanfax ™ 318 | 35 | 3.50 | 10 |
| Thickener | Methocel ™ E4M | 2.5 | 0.33 | 13.20 |
| Filler | Dispersed Plastic Pigment (RAP380NA) | 51.2 | 50 | 97.66 |
| pH Modifier | Ammonium hydroxide | 28 | -- to pH 9 - | |
| Coreactive Material: Epoxy | Ethylene glycol diglycidyl ether | 100 | 6 | 6 |

[a]DL595 and DL313 brand latexes, Methocel ™ E4M brand thickener, and RAP380NA dispersed plastic pigment were obtained from The Dow Chemical Company. Aquamix ™ 494 brand antioxidant was obtained from the Harwick Chemical Corporation. Stanfax ™ 318 brand froth stabilizer was obtained from Standard Adhesive & Chemical Company, Inc. Ethylene glycol diglycidyl ether (EGDGE) was obtained from Aldrich Chemical Company.

The latex formulation was frothed, shaped into a 0.5-inch (12 mm) thick sheet, and set as described in Example 2, with the exception that the froth was placed in the forced air oven at 150° C. for 30 min instead of 20 min. The resulting foam was sliced approximately in half along the thickness axis producing 0.25-inch (6 mm) sheets with large diameter cells (approximately 1.4 mm) on one surface and smaller diameter cells (approximately 100 microns) on the opposing surface. The foam was compressed in a hydraulic press under approximately 150 psig pressure reducing the foam thickness to approximately 1 mm. The compressed foam remained thin-till-wet.

Vertical Wicking was measured on the compressed foam in the manner described in the Test Procedures, using sample strips of approximately 28 cm length by 1 cm width cut from the compressed foam. Results are set forth in Table 6.

TABLE 6

Vertical Wicking Results for Example 4

| Time (minutes) | 2 | 10 | 30 | 60 |
|---|---|---|---|---|
| Height (cm) | 7.3 | 13.5 | 15 | 15 |

The unwetted foam thickness remained at about 1 mm, while the foam end in contact with the water expanded to approximately 5 mm in thickness.

It was seem that a latex polymer foam of this invention was capable of vertically wicking a 0.9 weight aqueous saline solution to a height of 15 cm, reaching a height of greater than 7 cm in 2 min.

EXAMPLE 5

A latex foam was prepared as in Example 4, with the exception that the foam was frothed, shaped, and cured into a sheet of 0.25 inch (6.3 mm) thickness. In contrast to Example 4, the foam was used as synthesized and was not sliced in half. The foam was compressed in a hydraulic press under approximately 150 psi pressure reducing the foam thickness to approximately 0.024 inches (0.6 mm). The compressed foam remained thin-till-wet.

Within 24 h of the foam, vertical wicking was measured in the manner described in Test Procedures with the results set forth in Table 7.

TABLE 7

Vertical Wicking for Example 5

| Time (minutes) | Vertical Wicking Ht. (cm) |
| --- | --- |
| 0.5 | 0.8 |
| 1 | 1.3 |
| 2 | 2.0 |
| 3 | 3.2 |
| 4 | 4.5 |
| 5 | 5.0 |
| 10 | 7.3 |
| 30 | 11.5 |
| 60 | 13.5 |
| 90 | 14.0 |

The physical properties of the foam composition, that is, stress at user break, percentage elongation at user break, and toughness, were measured on a sample of the compressed foam prior to wetting (dry) and after soaking in 0.9-percent aqueous saline solution (wet), in accordance with the Test Procedures. Results of the physical property measurements are shown in Table 8.

TABLE 8

Physical Properties (Durability)

| Polymer State | Stress at user break (psi) | % Elongation at user break | Toughness (psi) |
| --- | --- | --- | --- |
| Dry | 109.76 | 314.77 | 201.07 |
| Wet | 20.25 | 285.11 | 28.41 |

It was found that the polymer latex foam composition of this invention vertically wicked a saline solution to a height of nearly 14 cm in 60 min. The composition, in both dry and wet states, was found to exhibit good values of stress at user break, percentage elongation at user break, and toughness.

EXAMPLE 6

A latex formulation was prepared according to Table 9. The formulation was prepared by adding the components to a beaker in the order listed while mixing with a Cowles-type blade. Care was taken to minimize the amount of air entrained.

TABLE 9

Latex Froth Formulation for Example 6

| Component[a] | Name | % Solids | Dry Parts by weight | Wet Parts by weight |
| --- | --- | --- | --- | --- |
| Latex | DL595 | 51 | 100 | 195.31 |
| Anti-oxidant | Aquamix ™ 494 | 58 | 1.50 | 2.59 |
| Froth Stabilizer | Stanfax ™ 318 | 35 | 3.50 | 10 |
| Thickener | Methocel ™ E4M | 2.5 | 0.33 | 13.20 |
| pH Modifier | Ammonium hydroxide | 28 | -- pH 9 - | |
| Coreactive Material: Epoxy | Ethylene glycol diglycidyl ether | 100 | 6 | 6 |

TABLE 9-continued

Latex Froth Formulation for Example 6

| Component[a] | Name | % Solids | Dry Parts by weight | Wet Parts by weight |
| --- | --- | --- | --- | --- |

[a]DL595 and Methocel ™ E4M brand thickener were obtained from The Dow Chemical Company. Aquamix ™ 494 brand antioxidant was obtained from the Harwick Chemical Corporation. Stanfax ™ 318 brand froth stabilizer was obtained from Standard Adhesive & Chemical Company, Inc. Ethylene glycol diglycidyl ether (EGDGE) was obtained from Aldrich Chemical Company.

The latex formulation was frothed, shaped into a 0.25-inch (6 mm) thick sheet, and set as described in Example 1. The foam was compressed only slightly by hand to approximately 20 percent of its original thickness. The compressed foam remained thin-till-wet.

Vertical wicking measurements were done on the compressed foam, in the manner described in the Test Procedures, using a 15 cm long sample, instead of the typical 30 cm long sample. The compressed foam wicked a 0.9 weight percent aqueous saline solution 12 cm in 10 min. The saline solution had reached the top of the 15 cm strip within 60 min. The foam further demonstrated a free absorbent capacity of 18 g/g.

EXAMPLE 7

Latex foams were prepared as in Example 1 except the ratio of DL532 to DL313 were changed systematically. Increasing the levels of polymer with a higher glass transition increases the extent of compression after the compressive force is removed. The ratios of DL532/DL313 are 68/32, 50/50, 25/75 and 0/100 all other component were held constant. The height of the foams was measured. The foams were compressed as described in Example 1. The force was removed, and the foam allowed to recover. The resulting foam height was reported as a percentage of the original, non-compressed foam.

TABLE 10

Extent of Compression (% of uncompressed foam thickness)

| Ratio of DL 532/DL313 | 68/32 | 50/50 | 25/75 | 0/100 |
| --- | --- | --- | --- | --- |
| Foam height (after compression & recovery) | 29% | 27% | 22% | 13% |

This data shows the ability to control the thickness of the final compressed foam. The extent of compression is recorded as the percent of the original uncompressed foam.

What is claimed is:

1. A process for preparing a hydrophilic polymeric latex foam comprising:
   (a) frothing a formulation comprising a reactive latex polymer, the formulation being designed to produce a durable, conformable, hydrophilic, polymeric latex foam capable of acquiring and distributing fluids and capable of vertically wicking a 0.9 weight percent aqueous saline solution to a height of greater than about 5 cm;
   (b) drawing the frothed latex formulation into a desired shape;
   (c) setting the shaped latex formulation under conditions sufficient to prepare the aforementioned durable, conformable, hydrophilic, polymeric latex foam composition; and
   (d) optionally, compressing the latex foam under conditions sufficient to prepare a "thin-till-wet" foam composition.

2. The process of claim 1 wherein the latex polymer is selected from styrene/butadiene/acrylic acid and styrene/butadiene/glycidyl methacrylate latex polymers.

3. The process of claim 1 wherein the solids content of the reactive latex polymer in the formulation is greater than about 20 and less than about 80 weight percent, based on the total weight of the formulation.

4. The process of claim 1 wherein the latex formulation comprises a coreactive material which is soluble in water or in a water-miscible solvent or which is water dispersible, and which contains at least one carbon atom and which has at least two substituent groups which are coreactive with reactive groups on the latex polymer.

5. The process of claim 4 wherein the coreactive substituent groups are selected from (a) methylol groups which are attached to a nitrogen atom, (b) modified methylol groups which have been alkylated with an alcohol having from 1 to about 4 carbon atoms when such groups are attached to a nitrogen atom, (c) methylol groups when attached to the aromatic ring of a phenolic compound, (d) carboxyl groups, (e) primary amino groups, (f) secondary amino groups, (g) epoxy groups, and (h) zwitterionic functionalities.

6. The process of claim 4 wherein the coreactive material is selected from the group consisting of ethylene glycol diglycidyl ether, polyethylene glycol diglycidyl ether, and diethylene glycol diglycidyl ether.

7. The process of claim 4 wherein the coreactive material is present in an amount from greater than about 0 to less than about 100 parts coreactive material per one hundred parts solids, based on the reactive latex solids content.

8. The process of claim 1 wherein the formulation further comprises a foaming aid which is selected from sodium lauryl sulfate, sodium dodecyl sulfate, and mixtures thereof.

9. The process of claim 8 wherein the foaming aid is present in an amount from greater than about 0 to less than about 50 parts per one hundred parts solids, based on the weight of the reactive latex solids.

10. The process of claim 1 wherein the formulation further comprises a foam stabilizer which is selected from potassium oleate, disodium N-octyldecylsulfosuccinimate, and mixtures thereof.

11. The process of claim 10 wherein the foam stabilizer is present in a quantity greater than about 0 to less than about 50 parts per one hundred parts solids, based on the weight of the reactive latex solids.

12. The process of claim 1 wherein the formulation further comprises an acidifying or alkalizing agent, and the pH is adjusted to a value between about 7 and about 13.

13. The process of claim 1 wherein the formulation further comprises a thickener.

14. The process of claim 1 wherein the formulation further comprises a filler selected from the group consisting of talc, calcium carbonate, titanium dioxide, carbon black, redispersible latex, plastic pigments, fumed silica, hollow ceramic microspheres, and hollow glass microspheres.

15. The process of claim 14 wherein the filler comprises from greater than about 1 to less than about 100 parts per one hundred parts solids, based on the weight of the reactive latex solids.

16. The process of claim 1 wherein the formulation comprises a gelling agent.

17. The process of claim 1 wherein the formulation comprises a plasticizing component.

18. The process of claim 1 wherein the frothed latex formulation is drawn into a desired shape by (a) pouring or spreading into molds, (b) spreading on a flat tray or belt, (c) coating or laminating onto one or more substrates, or by (d) layering or blending two or more froths.

19. The process of claim 1 wherein the shaped configuration is set at a temperature greater than about 90° C. and less than about 200° C.

20. The process of claim 1 wherein, after setting, the foam is cut perpendicular to the thickness axis so as to obtain a foam having a gradient of cell sizes along the thickness axis from one surface to the opposing surface.

21. The process of claim 1 wherein the set shape is compressed under a pressure greater than about 28 psig (193 kPa) to less than about 700 psig (4,826 kPa).

22. The process of claim 1 wherein a tackifying agent is employed.

23. The process of claim 18 wherein the substrate and/or the latex are microapertured before or after curing.

24. The process of claim 1 wherein the latex foam is embossed.

25. The process of claim 1 wherein the latex foam comprises a honeycomb structure of carboxylate-rich material within the polymer wall.

* * * * *

UNITED STATES PATENT AND TRADEMARK OFFICE
CERTIFICATE OF CORRECTION

PATENT NO. : 6,627,670 B2
DATED : September 30, 2003
INVENTOR(S) : Steven W. Mork et al.

It is certified that error appears in the above-identified patent and that said Letters Patent is hereby corrected as shown below:

<u>Title page,</u>
Item [75], Inventors, replace "Steven M. Mork" with -- Steven W. Mork --.

Signed and Sealed this

Twenty-second Day of June, 2004

JON W. DUDAS
*Acting Director of the United States Patent and Trademark Office*